(12) United States Patent
Hill et al.

(10) Patent No.: US 11,857,723 B2
(45) Date of Patent: Jan. 2, 2024

(54) DEVICES AND METHODS FOR DELIVERING AIR TO A PATIENT

(71) Applicant: Garland Hill, Hiawassee, GA (US)

(72) Inventors: Garland Hill, Hiawassee, GA (US);
Jameson Joshua, Acworth, GA (US);
Stephen P. Chininis, Peachtree Corners, GA (US)

(73) Assignee: Garland Hill, Hiawassee, GA (US)

( * ) Notice: Subject to any disclaimer, the term of this patent is extended or adjusted under 35 U.S.C. 154(b) by 0 days.

(21) Appl. No.: 18/022,219

(22) PCT Filed: Oct. 4, 2021

(86) PCT No.: PCT/US2021/053376
§ 371 (c)(1),
(2) Date: Feb. 20, 2023

(87) PCT Pub. No.: WO2022/076311
PCT Pub. Date: Apr. 14, 2022

(65) Prior Publication Data
US 2023/0310771 A1    Oct. 5, 2023

Related U.S. Application Data

(60) Provisional application No. 63/088,205, filed on Oct. 6, 2020.

(51) Int. Cl.
*A61M 16/00*    (2006.01)
(52) U.S. Cl.
CPC .... *A61M 16/0048* (2013.01); *A61M 16/0072* (2013.01); *A61M 16/0003* (2014.02); *A61M 16/0078* (2013.01); *A61M 2016/0027* (2013.01)

(58) Field of Classification Search
CPC .......... A61M 16/0048; A61M 16/0078; A61M 16/0084; A61M 16/0073; A61M 16/0003
See application file for complete search history.

(56) References Cited

U.S. PATENT DOCUMENTS

| | | | |
|---|---|---|---|
| 6,595,212 B1 * | 7/2003 | Arnott | A61M 16/0006 128/204.23 |
| 2006/0272642 A1 | 12/2006 | Chalvignac | |
| 2013/0008444 A1 | 1/2013 | Chalvignac et al. | |
| 2017/0082116 A1 | 3/2017 | Nibu et al. | |
| 2018/0147377 A1 | 5/2018 | Hill | |
| 2019/0217029 A1 | 7/2019 | Lawrence | |

* cited by examiner

*Primary Examiner* — Margaret M Luarca
(74) *Attorney, Agent, or Firm* — Eversheds Sutherland (US) LLP

(57) ABSTRACT

Devices and methods for delivering air to a patient are provided. A device includes a first portion having a first airflow inlet and a sensor configured to sense airflow, the first portion defining a first airflow path, and a second portion comprising a second airflow inlet, an impeller, and an outlet for communicating airflow to a patient, the second portion defining a second airflow path. The device includes means for coupling the first portion and the second portion, such that the sensor sensing airflow in the first portion causes corresponding movement of the impeller, wherein the impeller is configured to impel air through the second airflow inlet and out of the outlet to the patient, upon movement of the impeller.

20 Claims, 12 Drawing Sheets

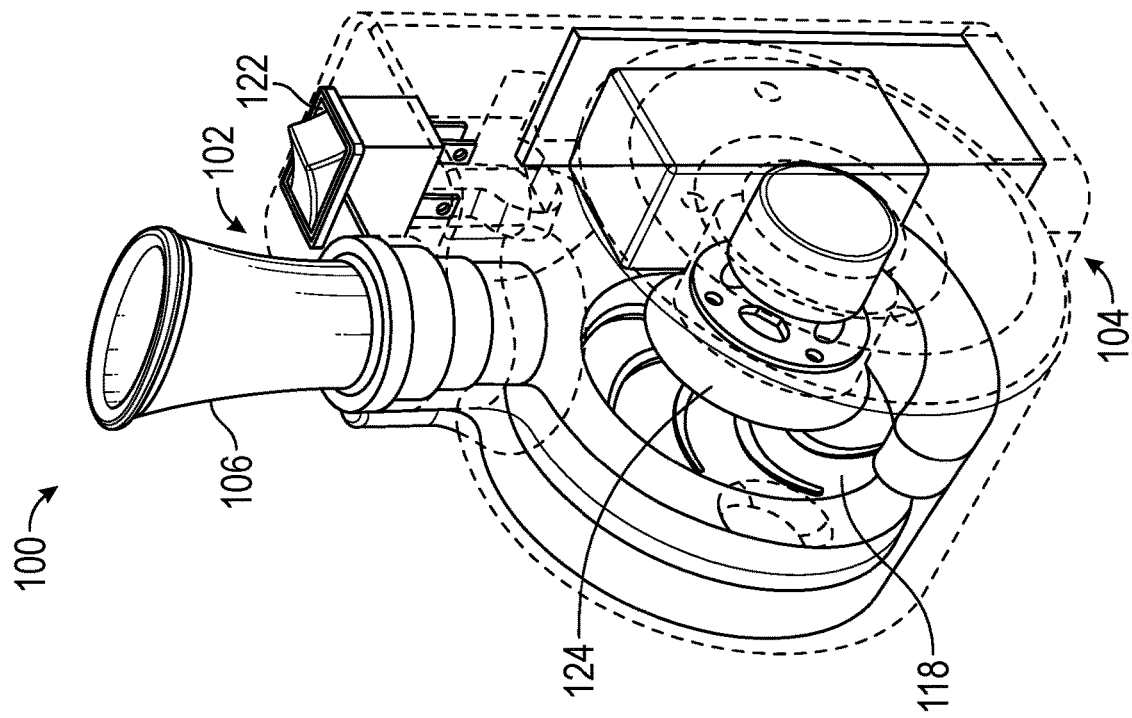
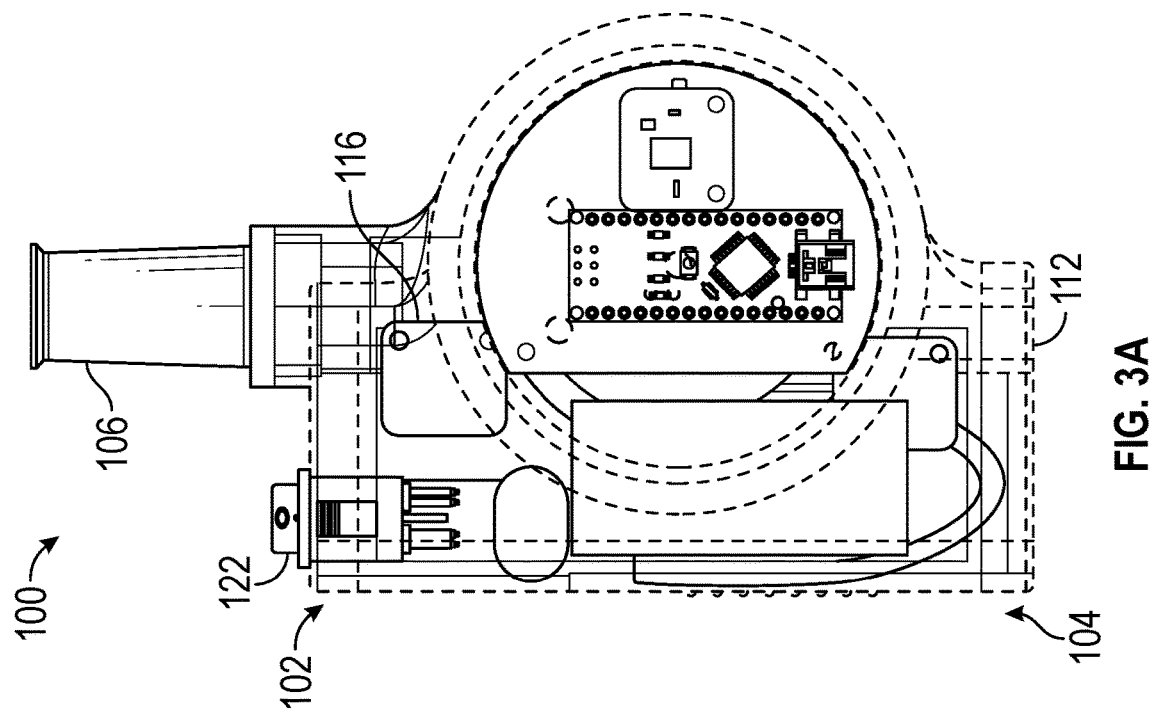
FIG. 3A
FIG. 3B

DEVICES AND METHODS FOR DELIVERING AIR TO A PATIENT

CROSS-REFERENCE TO RELATED APPLICATIONS

This application claims priority benefit of U.S. Provisional Patent Application No. 63/088,205, filed Oct. 6, 2020, which is incorporated by reference herein.

TECHNICAL FIELD

This disclosure relates generally to medical devices, and more particularly relates to devices and methods for delivering air to a patient.

BACKGROUND

Cardiopulmonary resuscitation (CPR) is an emergency medical procedure that traditionally combines chest compressions with artificial ventilation in an effort to provide oxygenated blood through the body, and to the brain, in patients where a prolonged loss of circulation places the patient at risk. The rescuer may provide artificial ventilation by either exhaling air into the subject's mouth or nose (e.g., mouth-to-mouth resuscitation) or using a device that pushes air into the subject's lungs (e.g., mechanical ventilation). Mechanical ventilation typically involves a ventilator machine or a medical professional compressing a bag valve mask or a set of bellows. However, such mechanical ventilation equipment is typically available only in hospitals or ambulances and can be cumbersome to transport to patients in the field.

Thus, mouth-to-mouth resuscitation is typically used by medical personnel in the field to provide artificial ventilation to patients. However, mouth-to-mouth resuscitation significantly increases the risk of contamination between the patient and medical personnel due to the exhaled air from the medical personnel being inhaled by the patient. Moreover, because the exhaled air from the medical personnel contains increased carbon dioxide, as compared to atmospheric air, the patient receives less oxygen during mouth-to-mouth resuscitation than through typical breathing, at a time when oxygen intake is critical.

Thus, improved devices and methods for delivering air to a patient in need of artificial ventilation are needed.

SUMMARY

In one aspect, devices for delivering air to a patient are provided, including a first portion having a first airflow inlet and a sensor configured to sense airflow, the first portion defining a first airflow path; a second portion having a second airflow inlet, an impeller, and an outlet for communicating airflow to a patient, the second portion defining a second airflow path; and means for coupling the first portion and the second portion such that the sensor sensing airflow in the first portion causes corresponding movement of the impeller, wherein the impeller is configured to impel air through the second airflow inlet and out of the outlet to the patient, upon movement of the impeller, and wherein the first and second airflow paths are not in fluid communication.

In another aspect, methods for delivering air to a patient are provided, including providing a device that includes: a first portion having a first airflow inlet and a sensor configured to sense airflow, the first portion defining a first airflow path; a second portion having a second airflow inlet, an impeller, and an outlet for communicating airflow to a patient, the second portion defining the second airflow path; and means for coupling the first portion and the second portion, such that the sensor sensing airflow in the first portion causes corresponding movement of the impeller; and providing air to the airflow inlet of the device to move the impeller, such that air is impelled through the second airflow inlet and out of the outlet to the patient, wherein the first and second airflow paths are not in fluid communication.

In yet another aspect, devices for delivering air to a patient are provided, including a housing; a first portion associate with the housing, the first portion having a first airflow inlet and an expandable bladder configured to expand within the housing in response to airflow from the first airflow inlet filling the expandable bladder, the first portion defining a first airflow path; and a second portion associated with the housing, the second portion having a second airflow inlet, and an outlet for communicating airflow to a patient, the second portion defining a second airflow path within the housing, wherein the device is configured such that upon expansion of the expandable bladder within the housing, air within the second airflow path is forced out of the outlet to the patient, and wherein the first and second airflow paths are not in fluid communication.

In another aspect, methods for delivering air to a patient are provided, including providing a device that includes: a housing; a first portion associated with the housing, the first portion having a first airflow inlet and an expandable bladder configured to expand within the housing in response to airflow from the first airflow inlet filling the expandable bladder, the first portion defining a first airflow path; and a second portion associated with the housing, the second portion having a second airflow inlet, and an outlet for communicating airflow to a patient, the second portion defining a second airflow path within the housing, and providing air to the airflow inlet of the device to move the impeller, such that air is impelled through the second airflow inlet and out of the outlet to the patient, wherein the first and second airflow paths are not in fluid communication.

BRIEF DESCRIPTION OF THE DRAWINGS

The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

FIGS. 3A-3D illustrate various x-ray views of the device of FIGS. 2A-2D.

DETAILED DESCRIPTION

Figure 1A:
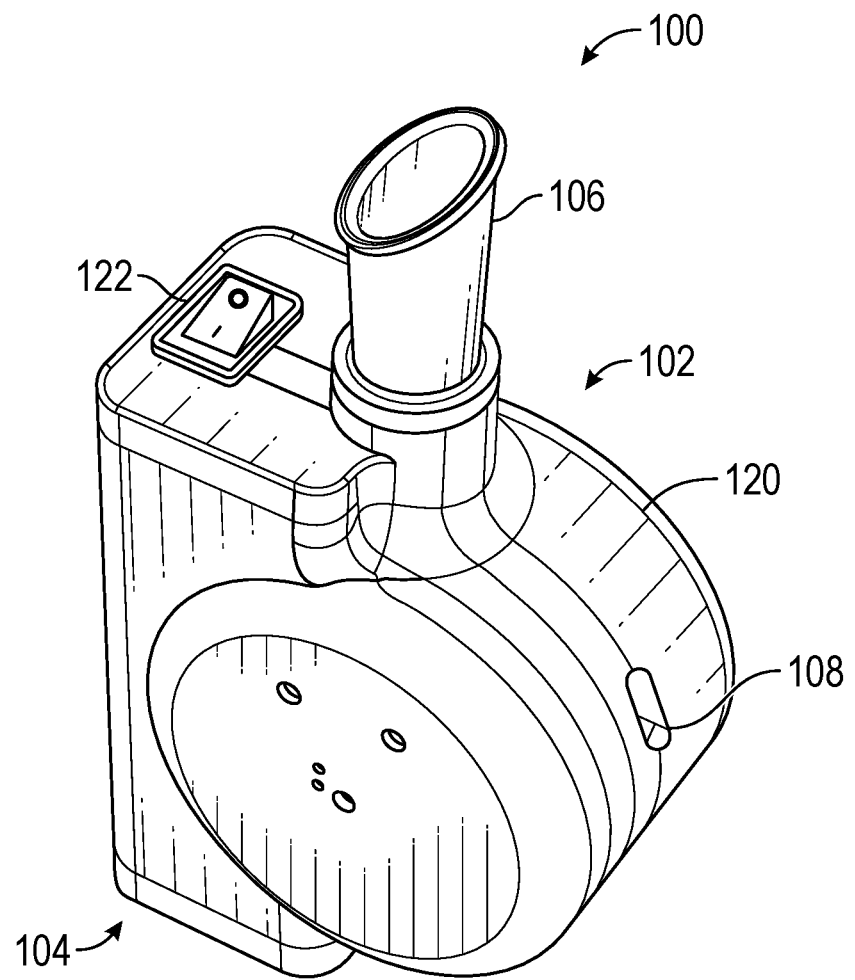
FIGS. 1A-1D are perspective views of an embodiment of a device for delivering air to a patient, in accordance with the present disclosure.
Figure 1B:
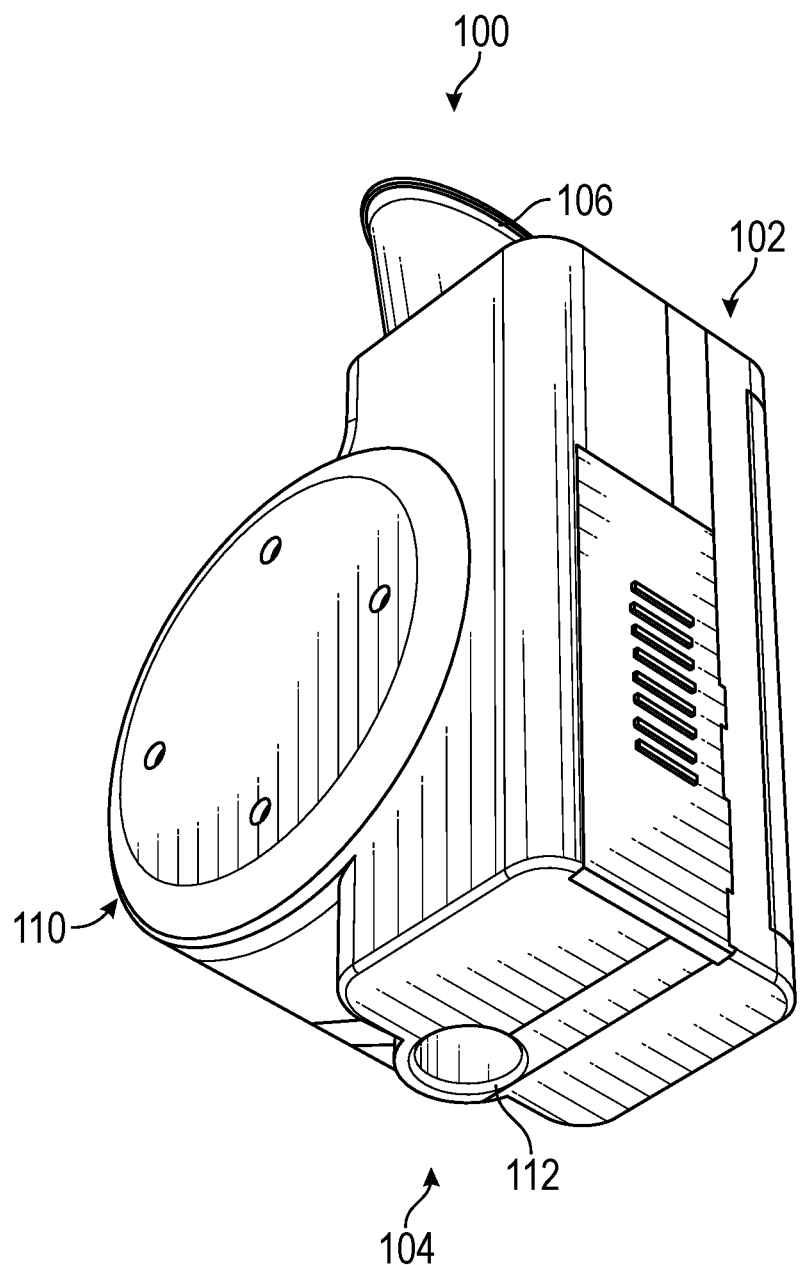
Figure 1C:
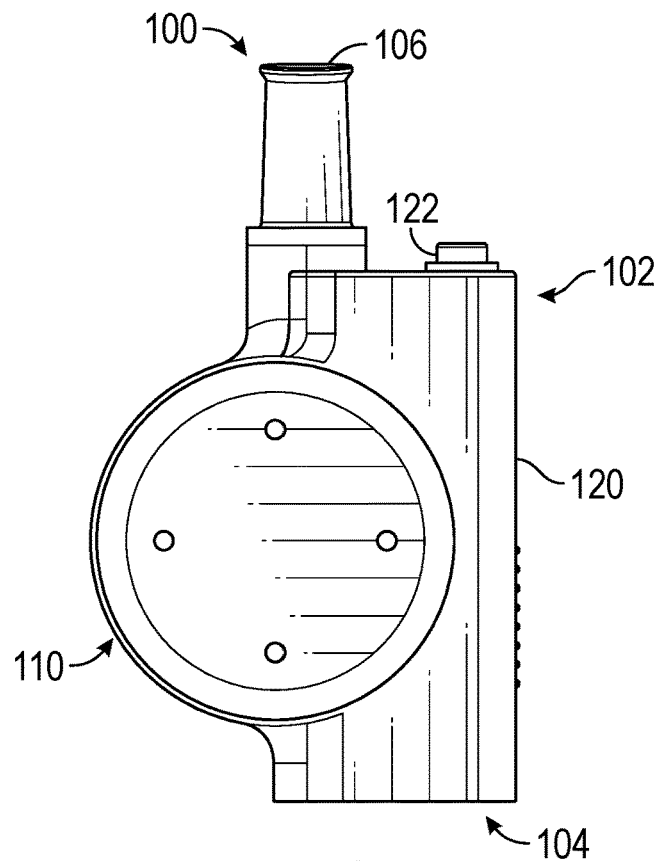
Figure 1D:
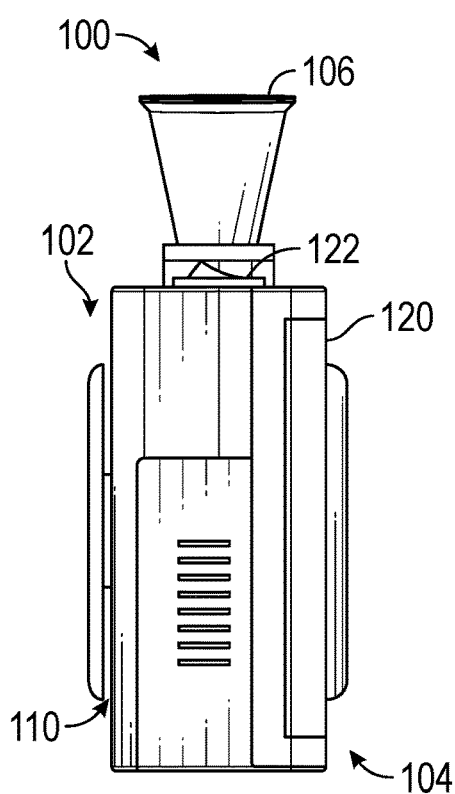
Figure 2A:
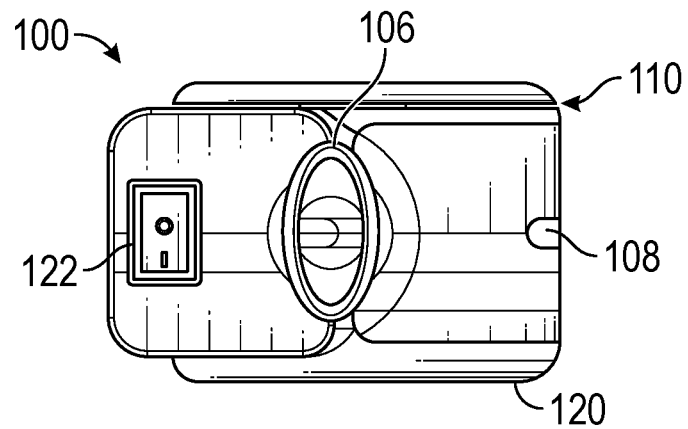
FIGS. 2A-2D illustrate various external views of an embodiment of a device for delivering air to a patient, in accordance with the present disclosure.
Figure 2B:
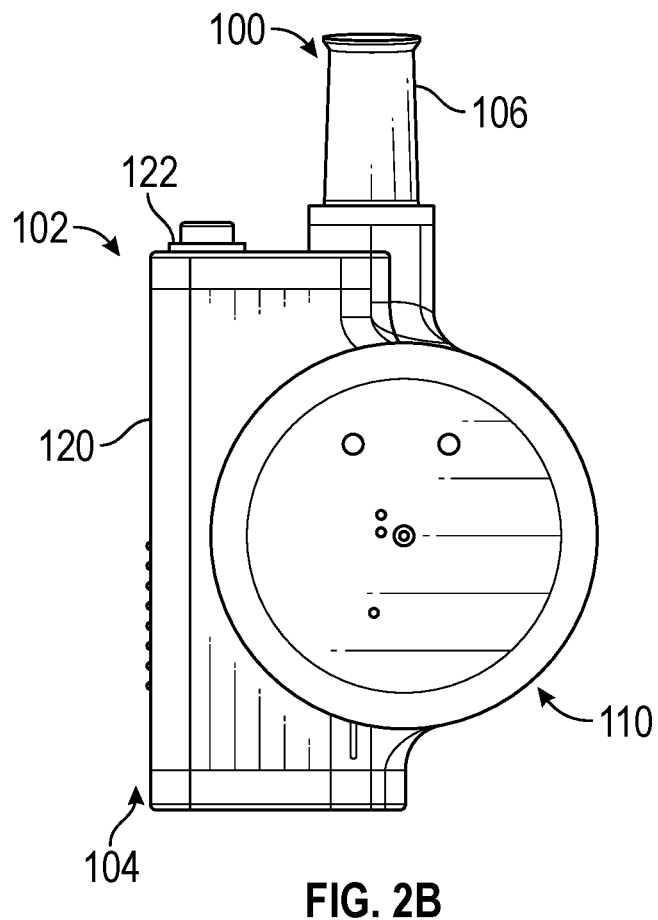
Figure 2C:
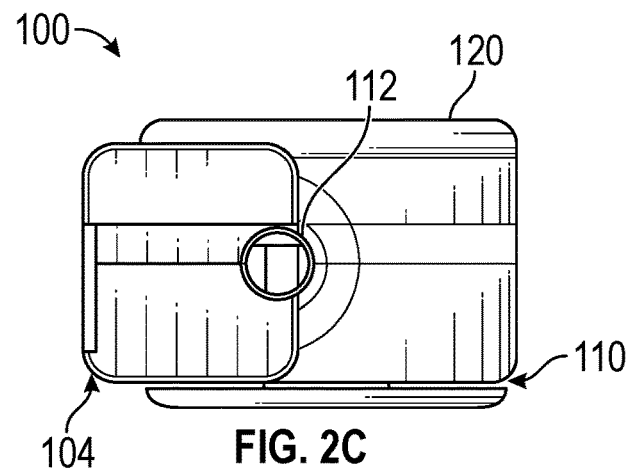
Figure 2D:
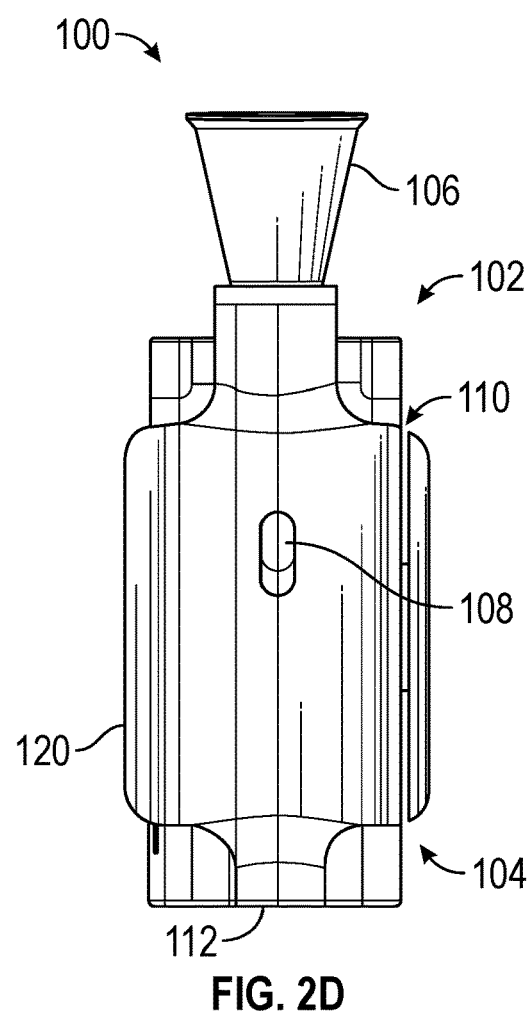
Figure 3D:
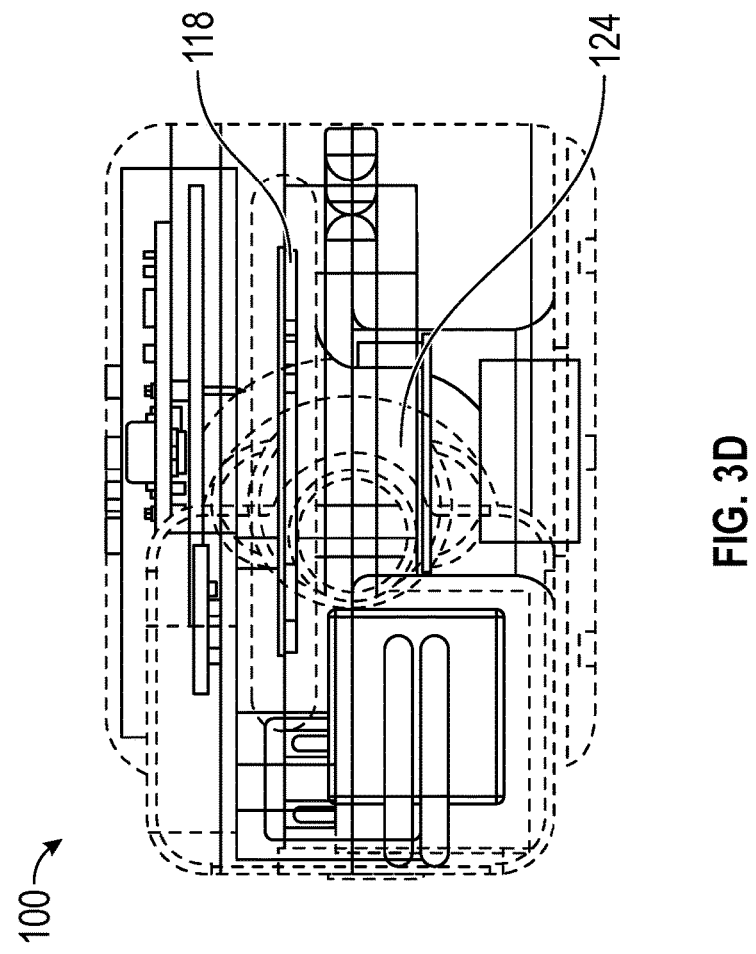
Figure 3C:
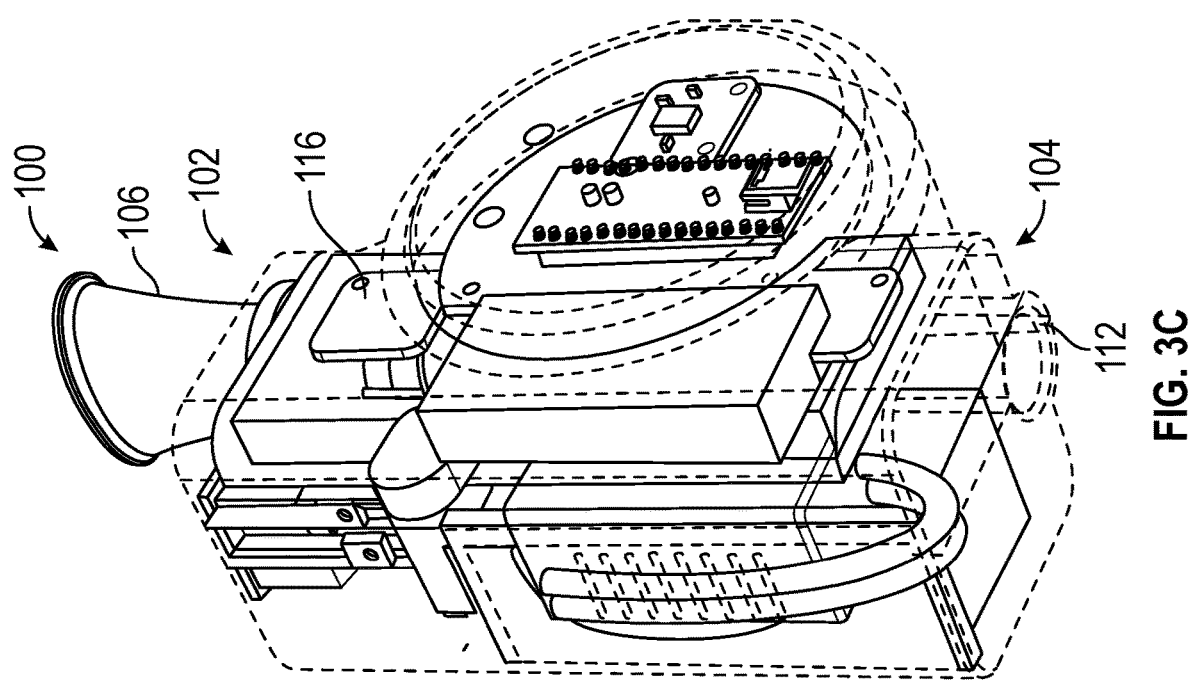
Figure 4A:
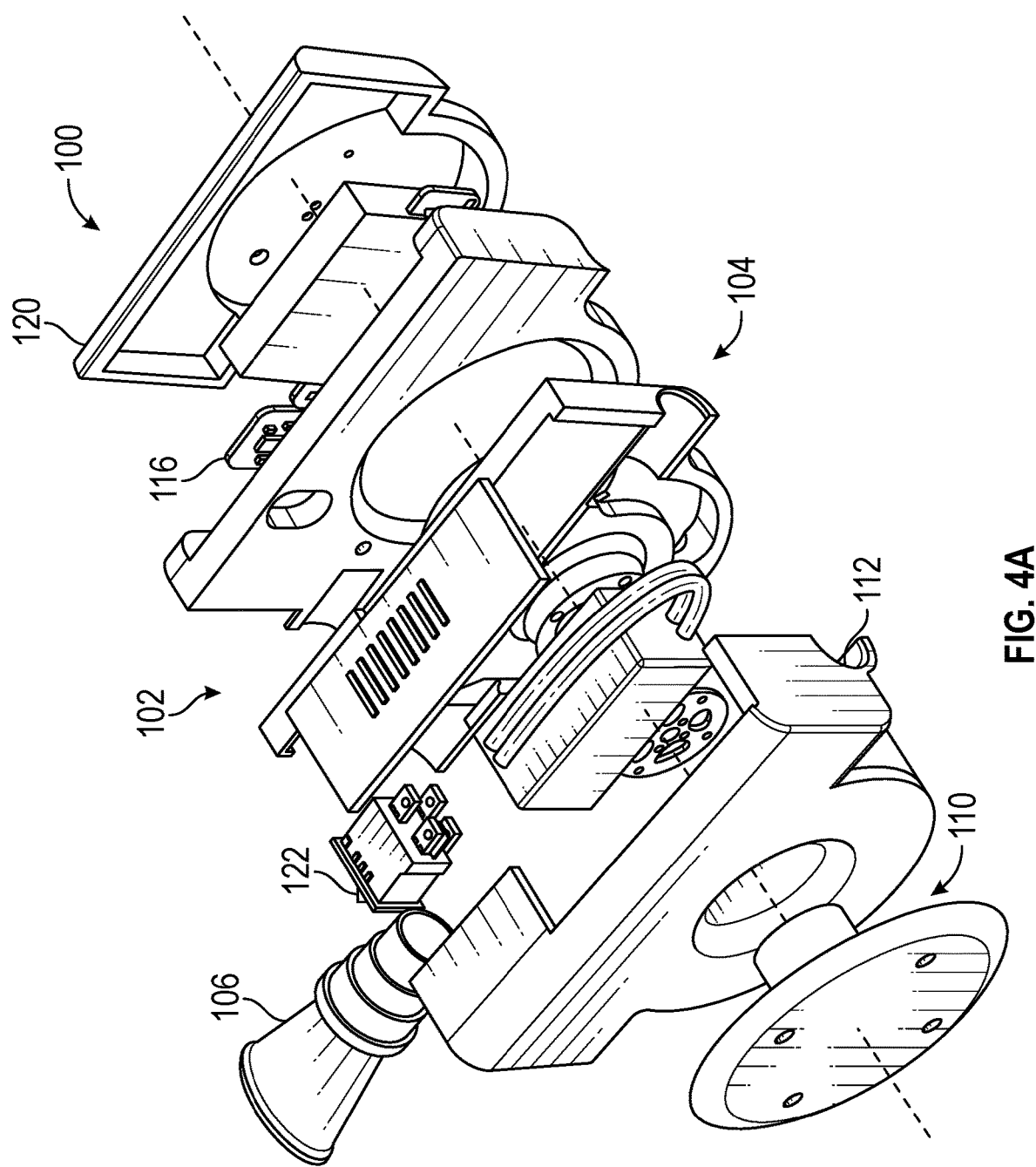
FIGS. 4A and 4B are exploded perspective views of the device of FIGS. 2A-2D.
Figure 4B:
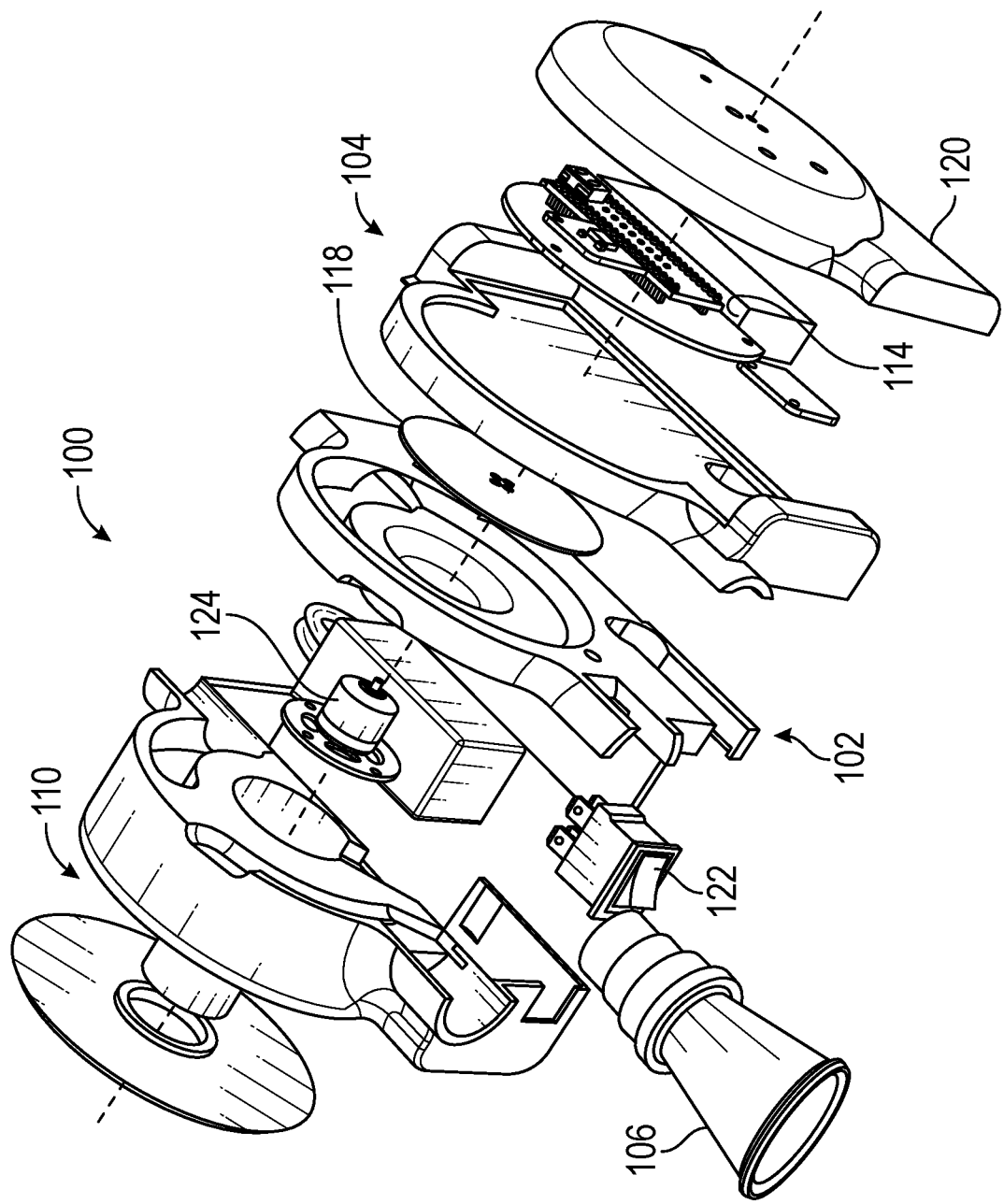

Devices and methods for delivering air to patients are provided herein. In certain embodiments, these devices and methods provide improved delivery of oxygen to a patient in need of artificial ventilation. U.S. Pat. No. 10,124,136 describes certain devices for delivering air to a patient utilizing a dual impeller system. The present disclosure provides improved devices and methods for delivery of oxygen to patients. Both manual and electronic systems are provided herein.

In one aspect, as shown in FIGS. 1A-5B, a device 100 for delivering air to a patient in need of artificial ventilation is provided. The device 100 includes a first portion 102 and a second portion 104. The first portion 102 has a first airflow inlet 106 and a sensor 116 that is configured to sense airflow provided to the first portion 102. The first portion 102 defines a first airflow path, including at least the first airflow inlet 106. In certain embodiments, the first airflow path further includes a first airflow outlet 108. The second portion 104 has a second airflow inlet 110, an impeller 118, and a second airflow outlet 112 for communicating airflow to the patient. The second portion 104 defines a second airflow path, including at least the second airflow inlet 110 and the second airflow outlet 112. The device 100 further includes means for coupling the first portion 102 and the second portion 104, such that the sensor 116 sensing airflow in the first portion drives corresponding movement of the impeller 118. The impeller 118 is configured to impel air through the second airflow inlet 110 and out of the second airflow outlet 112 to the patient, upon movement of the impeller 118. In certain embodiments, the first and second airflow paths are substantially not in fluid communication.

Thus, the device 100 is configured such that a user can exhale, or otherwise provide air, into the first airflow inlet 106 to effectuate movement of the impeller 118 that impels air from the surrounding atmosphere through the second portion 104 of the device and out through the second airflow outlet 112 to the patient. Moreover, because the airflow paths may not be in fluid communication (i.e., are not directly connected), the risk of contamination from the user to the patient is minimized, as the exhaled air is not provided directly to the patient. Instead, air from the atmosphere (which beneficially contains a higher volume of oxygen than exhaled air) is provided to the patient.

The means for coupling the first portion 102 and the second portion 104 may be any suitable means that would be understood by one of ordinary skill in the art, including various mechanical and electronic couplings. As used herein, the term "couples" and "coupling" are used broadly and refers to components being directly or indirectly connected to one another via any suitable fastening, connection, or attachment mechanism.

In some embodiments, as shown in FIGS. 1A-5B, the means for coupling the first portion 102 and the second portion 104 includes a controller 114 (e.g., microcontroller) that receives input from the sensor 116 and directs operation of the impeller 118, such as via a motor 124. In certain embodiments the first and second portions 102, 104 are contained within a single external housing 120. The housing 120 may be configured such that the first and second airflow paths are not in fluid communication. In other embodiments, the first and second portions 102, 104 may each include a separate housing that defines their respective airflow path, and the two housings may be coupled to one another. That is, the housings of the first and second portions 102, 104 may share one or more common walls or may be wholly separate from one another. The housing 120 illustrated in FIGS. 1-5 integrally forms both the first and second portions 102, 104; however, it should be understood that any suitable configuration, size and shape of the housings may be employed.

Figure 5A:
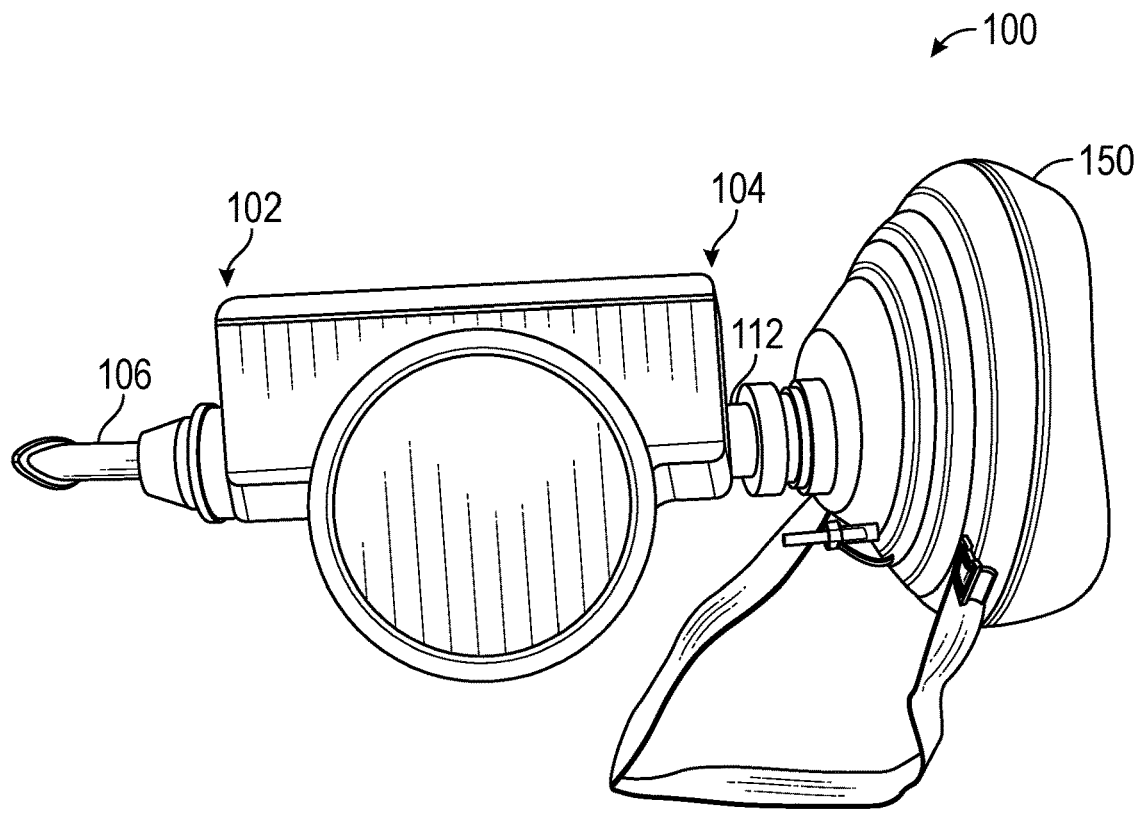
FIGS. 5A and 5B are perspective views of an embodiment of a device for delivering air to a patient, in accordance with the present disclosure.
Figure 5B:
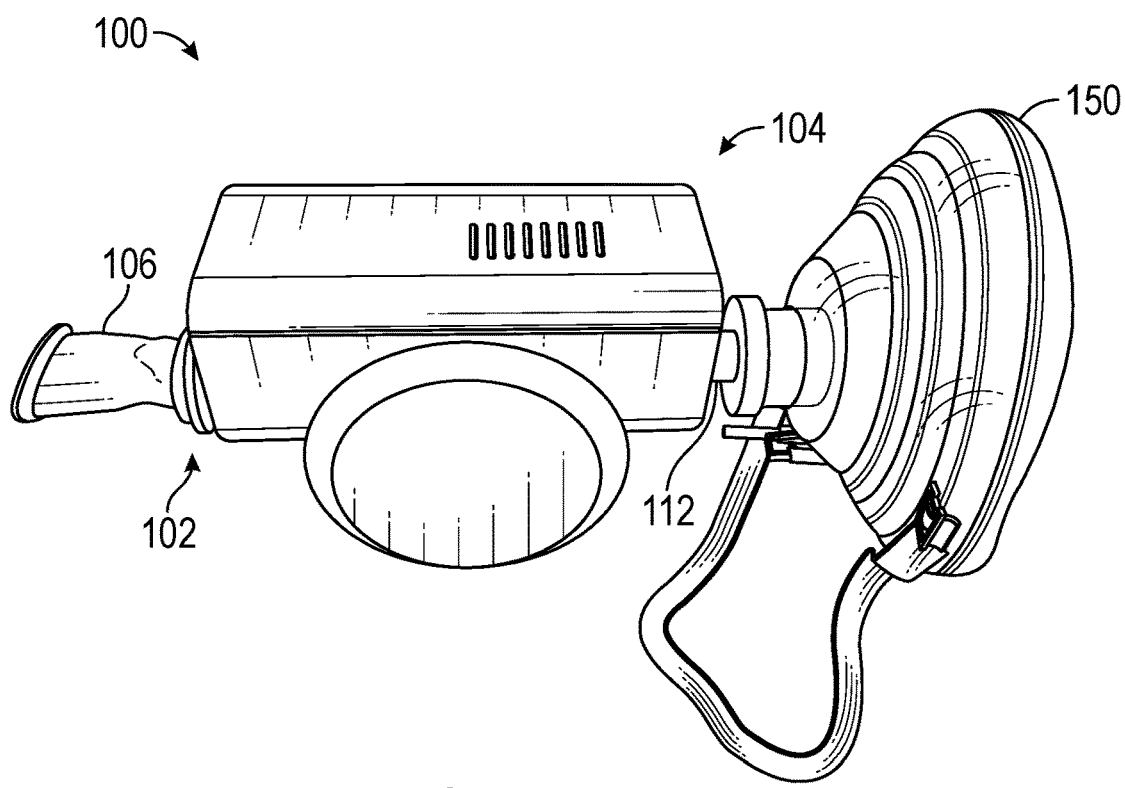

The airflow inlets and outlets may be formed integrally with or coupled to the housing(s) of the first and second portions. The airflow inlets and outlets may have any suitable size and shape. For example, the inlets and outlets may be provided in the form of spouts, tubes, openings, vents, channels, or other suitable configurations. Additionally, the inlets and outlets may optionally include threads, flanges, or other suitable attachment means for coupling the inlet or outlet to an external apparatus, such as an bag valve mask, a respiratory mask 150 (as shown in FIGS. 5A-5B), and/or an oxygen tank connector. For example, the second airflow outlet 112 of the second portion 104 of the device 100 may be configured for coupling to a respiratory mask 150 or pocket ventilator that is configured to fit over a patient's mouth. For example, the first airflow inlet 106 of the first portion 102 of the device 100 may be configured for coupling to a mechanically driven air source, such as a bag valve. For example, the second airflow inlet 110 of the second portion 104 of the device 100 may be configured for coupling to an oxygen tank, such as via an oxygen tube. In other embodiments, the second airflow inlet 110 is open to the atmosphere.

In some embodiments, the second portion 104 contains a filter configured to filter air impelled through the second airflow inlet 110. For example, the filter may be a screen or mesh, or a porous material designed to trap entrained particulate matter, keeping it from being introduced into the patient's lungs.

The sensor 116 may be any suitable sensor that is effective at sensing airflow of a rescuer's breath or other airflow traveling through the first airflow path. For example, the sensor 116 may be a sensor capable of sensing volumetric flow rate of the airflow, or a proxy therefor, traveling through the first airflow path. That is, the sensor may be configured to sense the intensity of the rescuer breath being delivered to the device. In certain embodiments, the sensor 116 is a pressure sensor, e.g., an air pressure sensor. The sensor may also include an anemometer or a switch that is triggered by a mechanical component that moves with airflow (e.g., an electromechanical, optical or magnetic switch).

In certain embodiments, the device is configured such that the corresponding movement of the impeller 118 is determined by the volumetric flow rate of the airflow sensed by the sensor 116. That is, the device may be configured such that the sensor senses the amount, intensity, timing and/or pattern of breath or other airflow provided to the first airflow path, and then generates a corresponding airflow in the second airflow path, to mimic the breathing in the first airflow path to the patient. Thus, a first responder or other medically trained personnel may provide rescue breathing to the first airflow path, such that corresponding airflow is delivered to the patient, without cross-contamination of the airflow paths.

In certain embodiments, the device is configured such that the corresponding movement of the impeller is initiated within about 200 to about 500 milliseconds, or less, of the sensor sensing airflow in the first portion. For example, a controller (e.g., microcontroller) may provide essentially immediate action of the impeller in response to the sensor sensing the breath or airflow in the first airflow path. In certain embodiments, the device contains a motor 124 configured to drive the impeller in response to the sensor sensing airflow in the first portion. For example, the device may be configured such that the motor is stopped within about 200 to about 500 milliseconds, or less, of the sensor failing to sense airflow in the first portion, when the motor is running.

For example, the controller and motor may have any suitable design and configuration. In some embodiments, the motor is a drum motor having a maximum rotational speed of about 30,000 rpm. In certain embodiments, the motor is designed to accelerate quickly enough to deliver sufficient air volume at a sufficient pressure to inflate the patient's lungs within 1 to 2 seconds and also to decelerate quickly enough to allow the elastic recoil of the patient's lungs to naturally exhaust the air. If the impeller were to keep moving, it would prevent the air in the patient's lungs from being exhaled before the delivery of the next breath. Therefore, the motor may be able to decelerate from max speed to zero rpm within about 1 second. The controller may be suitable to facilitate operation of the motor in response to the sensor sensing airflow in the first portion. The device may also include a power source, such as batteries, and a power switch 122 for turning the device on and off.

Any suitable impeller (e.g., rotor) designs may be used in the present devices 100. The impeller may be of any size, shape, and design suitable for providing the desired air intake through the second airflow inlet 110 and delivering the air out of the second airflow outlet 112 to the patient. Thus, in the second portion 104, any suitable impeller 118 that is capable of pulling in or impelling air through the second airflow path upon rotation or other movement of the impeller 118 may be used. Impellers having various fin designs may be used in the presently described devices 100. The fins of the impeller 118 may be angled or otherwise configured to achieve the desired inflow of air in response to movement of the second impeller 118. In some embodiments, the impeller 118 has a squirrel cage fan design.

While the device 100 is generally described with reference to impeller 118 throughout the disclosure, it should be understood that alternative air delivery mechanisms may be substituted for, or used in addition to, the impeller 118. For example, a motor-driven piston or bellow could be used instead of the impeller.

In certain embodiments, in addition to the above-described functionality utilizing a manual breathing or sensed-breathing/airflow mode, the device 100 also has an automatic mode, upon activation of which the device is configured to serially activate the impeller for a predetermined duration, to deliver a predetermined series of air pulses from the outlet to the patient. For example, the automatic mode may be programmed in accordance with recommending rescue breathing patterns. For example, the automatic mode may be configured to run the motor, and therefore provide a rescue breath to the patient, for a duration of 1 second, every 5 seconds. The automatic mode may provide these rescue breaths continuously until the mode is terminated or for a predetermined number of breaths. A single device may provide more than one programmed automatic modes, for various rescue breathing situations (e.g., child, adult, continuous).

Thus, in use in the sensed-breathing mode, a rescuer may exhale air or squeeze a bag mask to propel air through the first airflow path of the first portion 102 of the device 100. This exhaled air is measured by the sensor 116, which translates into motion of the second impeller 118. Motion of the second impeller results in air from the attached air source (e.g., atmosphere or another oxygen supply) being pulled into the second portion 104 and expelled from the outlet 112, and into an attached mask or patient mouth.

Figure 6:
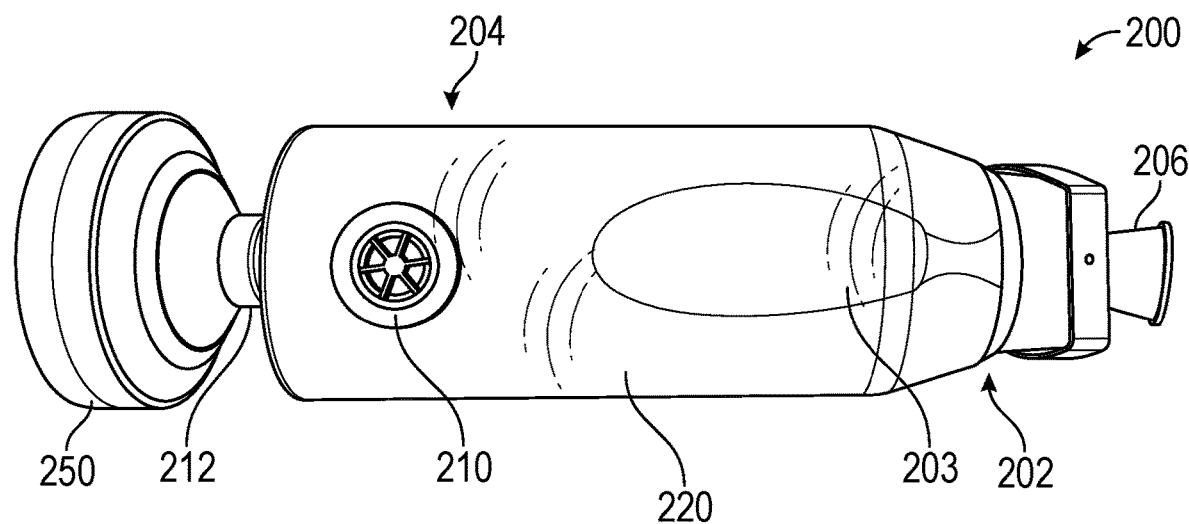
FIG. 6 is a perspective view of an embodiment of a device for delivering air to a patient, in accordance with the present disclosure.
Figure 7:
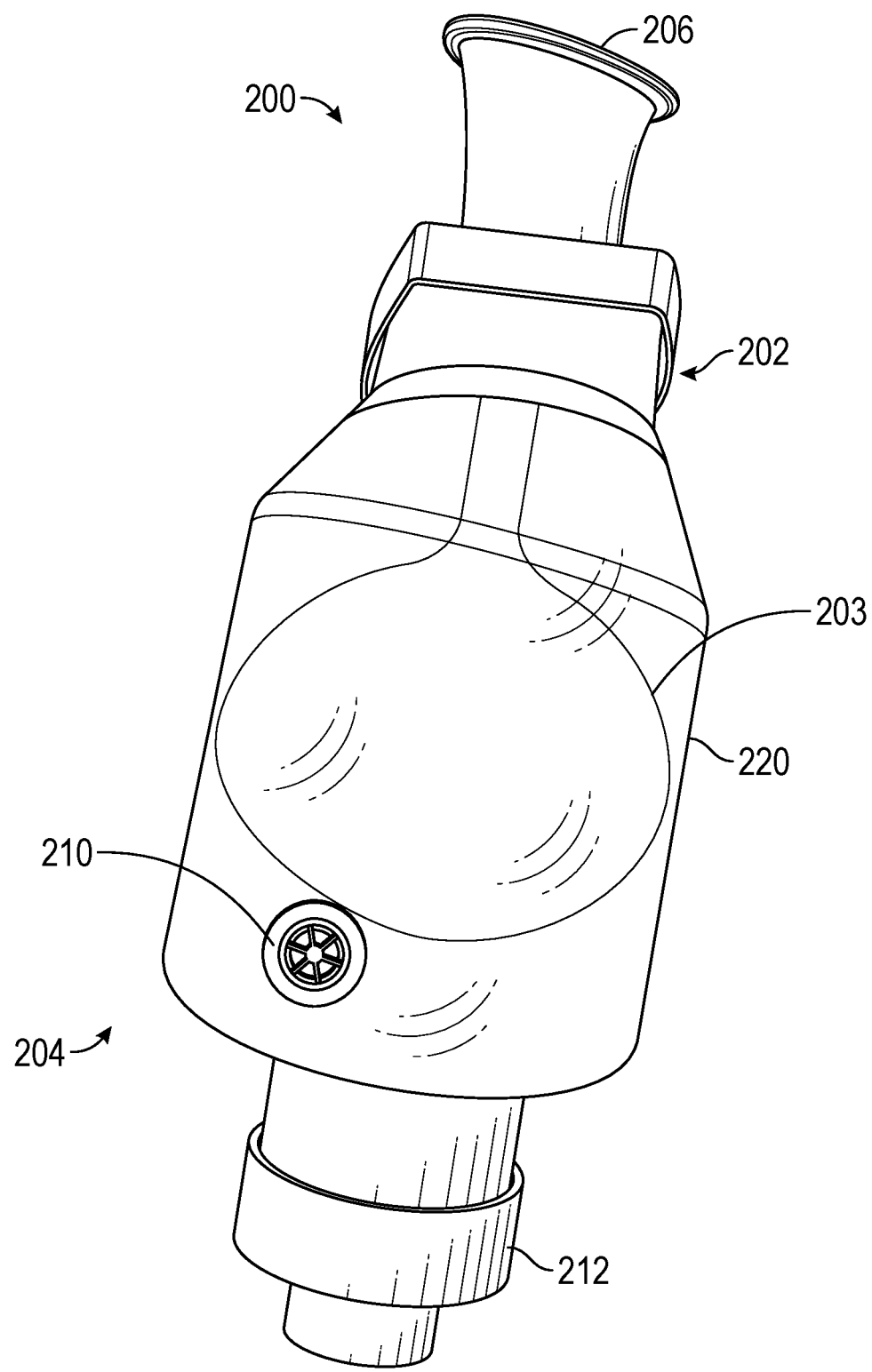
FIG. 7 is a perspective view of a device for delivering air to a patient, in accordance with the present disclosure.

In another aspect, a second design of a device 200 for delivering air to a patient, is provided. As illustrated in FIGS. 6 and 7, device 200 includes a housing 220, a first portion 202 associated with the housing 220 and having a first airflow inlet 206 and an expandable bladder 203 (e.g., elastic bladder) configured to expand within the housing in response to airflow from the first airflow inlet 206 filling the expandable bladder 203, the first portion 202 defining a first airflow path. The housing 220 may be formed of a suitable rigid material that is effective to maintain its inner volume, while the expandable bladder 203 may be formed of a suitable elastic or other material or design that allows for expansion and retraction of the bladder within the housing 220.

The device 200 also includes a second portion 204 associated with the housing 220 and having a second airflow inlet 210, and an outlet 212 for communicating airflow to a patient, the second portion 204 defining a second airflow path within the housing 220. The device 200 is configured such that upon expansion of the expandable bladder 203 within the housing 220, air within the second airflow path is forced out of the outlet 212 to the patient, via displacement of the air within the second airflow path out of the outlet 212. Air is replenished in the second airflow path via inlet 210 upon retraction of the expandable bladder 203. In certain embodiments, the first and second airflow paths are substantially not in fluid communication.

In certain embodiments, the second airflow inlet 210 is an aperture in a wall of the housing 220. In some embodiments, as shown in FIG. 6, the aperture has a one-way valve therein, to reduce airflow out of the housing via the aperture. In certain embodiments, the second portion 204 contains a filter configured to filter air that enters through the second airflow inlet 210.

In certain embodiments, as shown in FIG. 6, the outlet 212 is configured for coupling to a respiratory mask 250. In certain embodiments, the first airflow inlet 206 is configured for coupling to a removable mouthpiece. In certain embodiments, the first airflow inlet 206 is configured for coupling to a mechanically driven air source.

Thus, this device 200 design may provide a mechanical alternative to the electronic design described-above, allowing for the provision of rescue breathing without cross-contamination in situations in which a powered device may not be suitable (e.g., remote or long term first aid kits).

The components of the devices 100, 200 described herein may be formed from any suitable materials or combination of materials. For example, the housings, impeller, and mechanical coupling may be formed from suitable materials such as plastics and metals. In certain embodiments, the device 100, 200 is configured for one-time, disposable use. In other embodiments, the device 100, 200 is configured to be reusable and can be sanitized without harming the device components.

In other aspects, methods for delivering air to a patient are provided. For example, the methods may include providing air to the airflow inlet of a device 100 having any configuration described herein to be sensed by the sensor and cause movement of the impeller, such that air is impelled through the second airflow inlet and out of the outlet to the patient. For example, the air may be provided to the first airflow inlet of the device via rescue breathing or a mechanically driven air source coupled to the first airflow inlet of the first portion 102.

In certain embodiments, methods for delivering air to a patient involve providing a device 100 as described herein, including any combination of features described herein, and then providing air to the airflow inlet of the device to move the impeller, such that air is impelled through the second airflow inlet and out of the outlet to the patient.

In other embodiments, methods for delivering air to a patient involve providing a device 200 as described herein, including any combination of features described herein, and then providing air to the airflow inlet of the device to expand the expandable bladder within the housing, such that air within the second airflow path is forced out of the outlet to the patient.

In further aspects, kits are provided, including a device 100, 200 having any configuration described herein and a respiratory mask 150, 250 configured for attachment to the outlet of the second portion 112, 212 of the device 100, 200 and/or a removable mouthpiece configured for attachment to the first airflow inlet 106, 206.

Thus, the presently described devices and methods beneficially provide air to a patient via a rescuer exhaling (or pumping a bag valve, etc.), while reducing the risk of contamination between the patient and rescuer, due to the exhaled air from the medical personnel being directed away from the patient, while clean air from the atmosphere or another oxygen supply is inhaled by the patient. Because the exhaled air from the rescuer contains increased carbon dioxide, as compared to atmospheric air, the patient receives more oxygen than as compared to during mouth-to-mouth resuscitation, at a time when oxygen intake is critical. Moreover, the barrier between the two portions of the device (i.e., the portion that the rescuer contacts and the portion that the patient contacts) limits the potential exposure of the rescuer to regurgitation from the patient.

Further, the device of the present disclosure is compact and simple to use, such that it may be easily transported by medical personnel into the field and/or may be provided at first aid stations/kits at various locations, such as at emergency stations in workplaces.

While the disclosure has been described with reference to a number of example embodiments, it will be understood by those skilled in the art that the disclosure is not limited to such disclosed embodiments. Rather, the disclosed embodiments can be modified to incorporate any number of variations, alterations, substitutions, or equivalent arrangements not described herein, but which are commensurate with the spirit and scope of the disclosure.

What is claimed is:

1. A device for delivering air to a patient, comprising:
   a first portion comprising a first airflow inlet and a sensor configured to sense airflow, the first portion defining a first airflow path;
   a second portion comprising a second airflow inlet, an impeller, and an outlet for communicating airflow to a patient, the second portion defining a second airflow path; and
   means for coupling the first portion and the second portion, such that the sensor sensing airflow in the first portion causes corresponding movement of the impeller,
   wherein the impeller is configured to impel air through the second airflow inlet and out of the outlet to the patient, upon movement of the impeller, and
   wherein the first and second airflow paths are not in fluid communication.

2. The device of claim 1, wherein the sensor is a pressure sensor.

3. The device of claim 1, wherein the sensor is capable of sensing a volumetric flow rate of the airflow or a proxy therefor, wherein the device is configured such that the corresponding movement of the impeller is determined by the volumetric flow rate of the airflow sensed by the sensor.

4. The device of claim 1, wherein the device is configured such that the corresponding movement of the impeller is initiated within about 200 to about 500 milliseconds of the sensor sensing airflow in the first portion.

5. The device of claim 1, further comprising a motor configured to drive the impeller in response to the sensor sensing airflow in the first portion, wherein the device is configured such that the motor is stopped within about 200 to 500 milliseconds of the sensor failing to sense airflow in the first portion, when the motor is running.

6. The device of claim 5, further comprising a controller to facilitate operation of the motor in response to the sensor sensing airflow in the first portion.

7. The device of claim 1, comprising an automatic mode, upon activation of which the device is configured to serially activate the impeller for a predetermined duration, to deliver a predetermined series of air pulses from the outlet to the patient.

8. The device of claim 1, further comprising a housing for the first and second portions.

9. The device of claim 1, wherein the outlet is configured for coupling to a respiratory mask.

10. The device of claim 1, wherein the first airflow inlet is configured for coupling to a removable mouthpiece.

11. The device of claim 1, wherein the first airflow inlet is configured for coupling to a mechanically driven air source.

12. The device of claim 1, wherein the second airflow inlet is configured for coupling to an oxygen tank.

13. The device of claim 1, wherein the second portion further comprises a filter configured to filter air impelled through the second airflow inlet.

14. A device for delivering air to a patient, comprising:
   a housing;
   a first portion associated with the housing, the first portion comprising a first airflow inlet and an expandable bladder configured to expand within the housing in response to airflow from the first airflow inlet filling the expandable bladder, the first portion defining a first airflow path; and
   a second portion associated with the housing, the second portion comprising a second airflow inlet, and an outlet for communicating airflow to a patient, the second portion defining a second airflow path within the housing,
   wherein the device is configured such that upon expansion of the expandable bladder within the housing, air within the second airflow path is displaced and forced out of the outlet to the patient, and
   wherein the first and second airflow paths are not in fluid communication.

15. The device of claim 14, wherein the second airflow inlet comprises an aperture in a wall of the housing, wherein the aperture has a valve therein, to reduce airflow out of the housing via the aperture.

16. The device of claim 14, wherein the outlet is configured for coupling to a respiratory mask.

17. The device of claim 14, wherein the first airflow inlet is configured for coupling to a removable mouthpiece.

18. The device of claim 14, wherein the first airflow inlet is configured for coupling to a mechanically driven air source.

19. The device of claim 14, wherein the second airflow inlet is configured for coupling to an oxygen tank.

20. The device of claim 14, wherein the second portion further comprises a filter configured to filter air that enters through the second airflow inlet.

* * * * *